United States Patent [19]

Van Heugten et al.

[11] Patent Number: 5,120,319
[45] Date of Patent: Jun. 9, 1992

[54] FLASH TUBE FOR INTRAVENOUS CATHETER

[75] Inventors: Anthony Y. Van Heugten, Tampa; Julian E. Cannon, Brandon, both of Fla.

[73] Assignee: Critikon, Inc., Tampa, Fla.

[21] Appl. No.: 721,809

[22] Filed: Jun. 26, 1991

[51] Int. Cl.⁵ .................................... A61M 5/178
[52] U.S. Cl. ................................ 604/168; 604/900
[58] Field of Search ............ 604/168, 169, 900, 164, 604/166, 126

[56] References Cited

U.S. PATENT DOCUMENTS

| | | | |
|---|---|---|---|
| 4,108,175 | 8/1978 | Orton | 604/900 |
| 4,710,173 | 12/1987 | McFarlane | 604/168 |
| 4,828,548 | 5/1989 | Walter | 604/168 |
| 4,908,021 | 3/1990 | McFarlane | 604/168 |
| 4,917,669 | 4/1990 | Bonaldo | 604/164 |
| 4,961,729 | 10/1990 | Vaillancourt | 604/168 |
| 5,000,740 | 3/1991 | Ducharme et al. | 604/168 |
| 5,032,116 | 7/1991 | Peterson et al. | 604/168 |

Primary Examiner—Cary E. O'Connor
Attorney, Agent, or Firm—Paul A. Coletti

[57] ABSTRACT

A catheter device is disclosed which contains a catheter in an insertion needle. The insertion needle is attached to a needle hub which contains a flash chamber. Within the flash chamber the proximal end of the needle is connected to a clear plastic tube so that flash is initially determined in this tube; overflow flash is then caused to flow into the larger flash chamber from the flash tube.

12 Claims, 2 Drawing Sheets

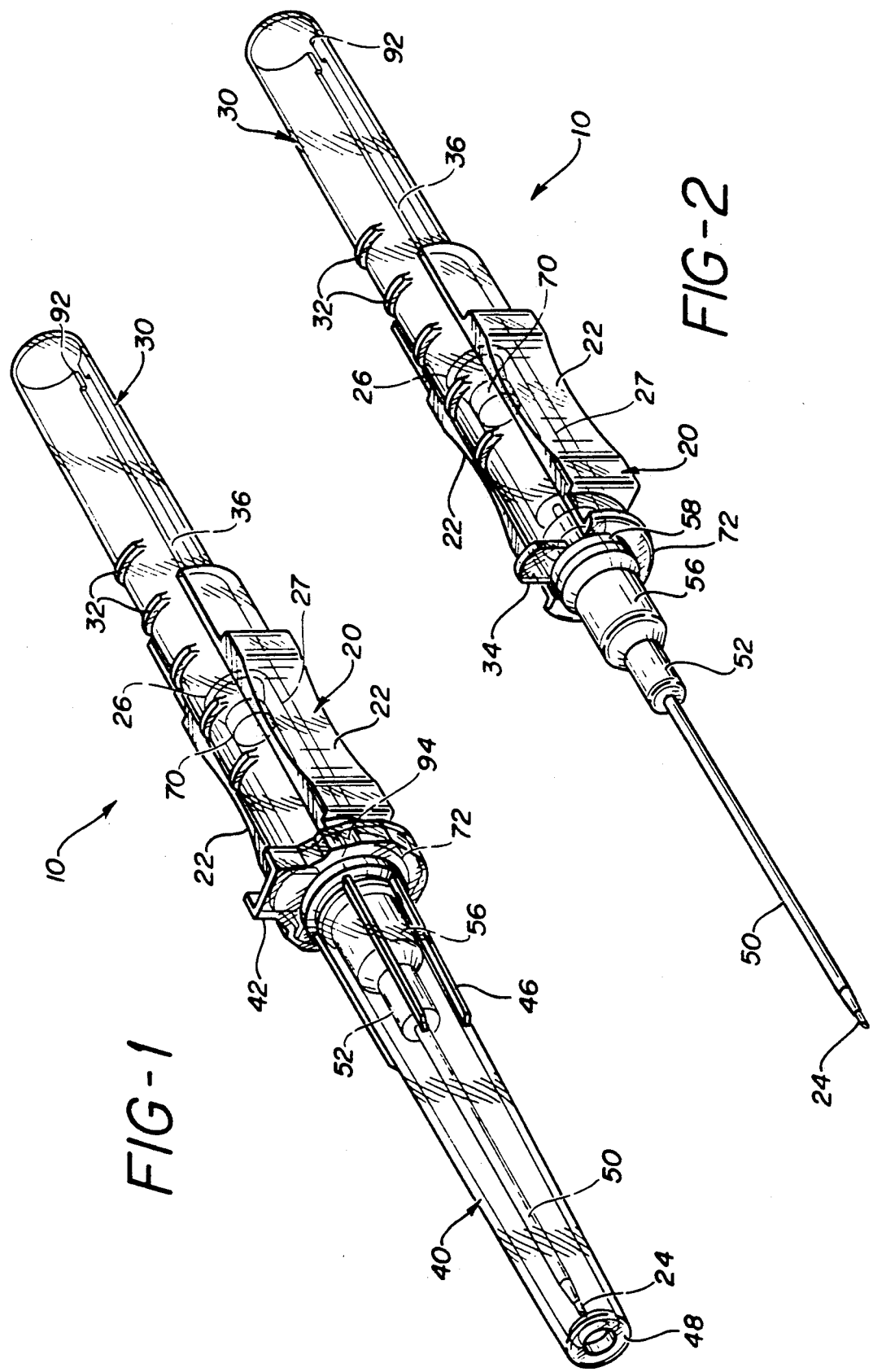

FLASH TUBE FOR INTRAVENOUS CATHETER

FIELD OF THE INVENTION

Generally this invention relates to intravenous catheters. More specifically, this invention relates to intravenous catheters which use a flash chamber for determining the puncture of a vein. Most specifically, this invention relates to intravenous catheters which have an enhanced flash indication chamber

BACKGROUND OF THE INVENTION

This invention relates to intravascular (I.V.) catheters and, in particular, to I.V. catheter assemblies which cover the needle point after use to prevent accidental injury from used needles.

Intravenous catheters for the infusion of fluids into the peripheral veins of a patient are one of the most common devices used in I.V. therapy I.V. catheters may be produced in two general forms: through-the-needle catheters, in which a catheter is threaded through the needle cannula and into the vein of a patient, and over-the-needle catheters, in which the needle and concentric outer catheter are inserted into the vein and the needle is withdrawn through the emplaced catheter.

A typical over-the-needle I.V. catheter assembly requires the user to remove and then dispose of a contaminated needle after the needle tip and catheter are properly located in a blood vessel of a patient Once the needle is withdrawn from the catheter, the user's immediate priorities are infusion set connection and site preparation, including the taping of the catheter to the patient. Because of the urgency of these procedures, the needle is normally just dropped conveniently nearby and then retrieved later. Since the needle at this time is exposed and located close to where the user is completing work with the catheter, accidental self-inflicted needle injuries are not uncommon. For reasons of the desirability of protecting the user from exposure to blood borne disease such as hepatitis and AIDS, there is an increasing need to protect the user from accidental needle injury.

A catheter design which is directed toward this need is shown in U.S. Pat. No. 4,762,516. The catheter shown in this application includes an elongate body which houses a sliding needle guard. In use, the needle with its surrounding catheter tube is inserted through the skin of a patient until the tip of the needle is located in a blood vessel, a position detected by a small flow of blood through the needle and into the flash chamber of the catheter The user then advances a tab on the top of the needle guard to simultaneously thread the catheter tube into the blood vessel and begin the retraction of the needle from the catheter tube. As the needle is withdrawn from the emplaced catheter, the advance of the tab slides the needle guard out of the housing and along the needle, until the distal end of the guard covers the needle tip and the proximal end of the guard locks in the elongate body. The needle and guard may then be set aside with the needle tip fully protected.

While the arrangement described in this patent application can provide full protection against accidental needle injury, it would be desirable to provide such a catheter in a smaller, smoothly operating configuration which can be readily manipulated by small hands. In this invention, a catheter assembly with needle guard is provided with a semi-tubular needle housing that is open on the upper surface. Located within the housing is a flash chamber with a needle extending from the distal end of the chamber and beyond the distal end of the housing. A tubular needle guard is located for distal movement within the semi-tubular needle housing, and has a distal opening through which the needle extends. The bottom of the needle guard is slotted to fit around the base of the flash chamber. At the rear of the needle guard slot is a portion of a locking mechanism which will engage with and lock in the needle housing when the needle guard is extended to cover the needle.

When an I.V. catheter is inserted into the patient, the user must have an indicator of some sort to signal successful entry of the introducer needle into the vein. The indicator is known as flashback and takes place in the flash chamber. Upon successful entry, the blood must travel through the length of the hollow needle and into a clear or translucent chamber opposite the penetrating end of the needle. The appearance of blood in this chamber is the flashback, and the chamber itself is the flash chamber. Once blood appears in the flash chamber, the user stops advancing the needle, and begins the process of threading the catheter tube into the vein.

It is important that the user see the flashback immediately otherwise there is a risk of continuing the needle advancement through the other side of the vein, without knowing that at one time they were already in it.

In most cases, a flash chamber with a large volume is best. One of the advantages of a large chamber is that it takes a period of time to fill the chamber, giving the user the opportunity to verify the continuation of blood flow. This ensures they are still inside, and have not penetrated through the opposite side of the vein.

In the small veins, when using the small needles, quick flashback and quick reaction speed are more important than when in larger veins. This is not only because the smaller veins are more fragile, but also there is less distance for the needle to travel before passing through the vein.

Unfortunately, the flashback is most difficult to see when using these small needle sizes with the typical large flash chamber design used today.

When dealing with very small needle sizes, the flashback can sometimes be no more than a small drop of blood. When only a small drop of blood presents itself, it can be difficult to see in the large flash chamber. In this situation, there is greater risk that the user will not see the blood becoming visible and react quickly enough to stop advancing the needle in time.

If the flash chamber were much smaller in diameter, the blood would be more visible in the cases of small flashback volumes. Yet, doing so would make the flash chamber unsuitable for use with higher volume flashback. Because the rate of flashback is unpredictable, and higher flashback volumes are more common than low flashback volumes, it would hinder more usages than it would help.

SUMMARY OF THE INVENTION

Accordingly, it is an object of the invention to provide a catheter device with improved flashback.

It is another object of the invention to provide a catheter device where flashback is enhanced even in catheter devices containing small diameter needles sizes.

It is yet another object of the invention to provide a flash chamber containing an improved flashback enhancement device incorporated therein, so that it is adaptable to presently preferred designs.

These and other objects of the invention are described for a catheter device which contains a catheter for insertion into a patient and where the catheter has a tubular center into which is emplaceable an insertion needle. The needle is hollow and cylindrical and is attached to a needle hub. The sharpened distal end is inserted into the catheter and then into the patient. The proximal end of the needle is engaged within the needle hub. The needle hub is connected to a flash chamber which is formed from a hollow clear plastic tube. The insertion needle end is surrounded by the hollow interior of the flash chamber. Finally, there is a flash tube connected to the proximal end of the needle within the flash chamber. The outer diameter of the flash tube is much smaller than the flash chamber and therefore permits the tube to fit within the flash chamber. Blood is capable of flowing through the punctured vein into the needle and then into the tube. Thereafter, once the tube is filled, overflow blood is capable of flowing into the flash chamber. Thus, after the enhanced needle device functions, the flash chamber operates as in typical flash chamber designs.

These and other objects of the invention will be better understood from the enclosed Detailed Description of the Drawings when taken in connection with the Detailed Description of the Invention.

DETAILED DESCRIPTION OF THE DRAWINGS

FIG. 1 is a perspective view of a typical catheter device useful with the present invention;

FIG. 2 is an assembly view of the catheter device useful with the present invention;

DETAILED DESCRIPTION OF THE INVENTION

Figure 3:
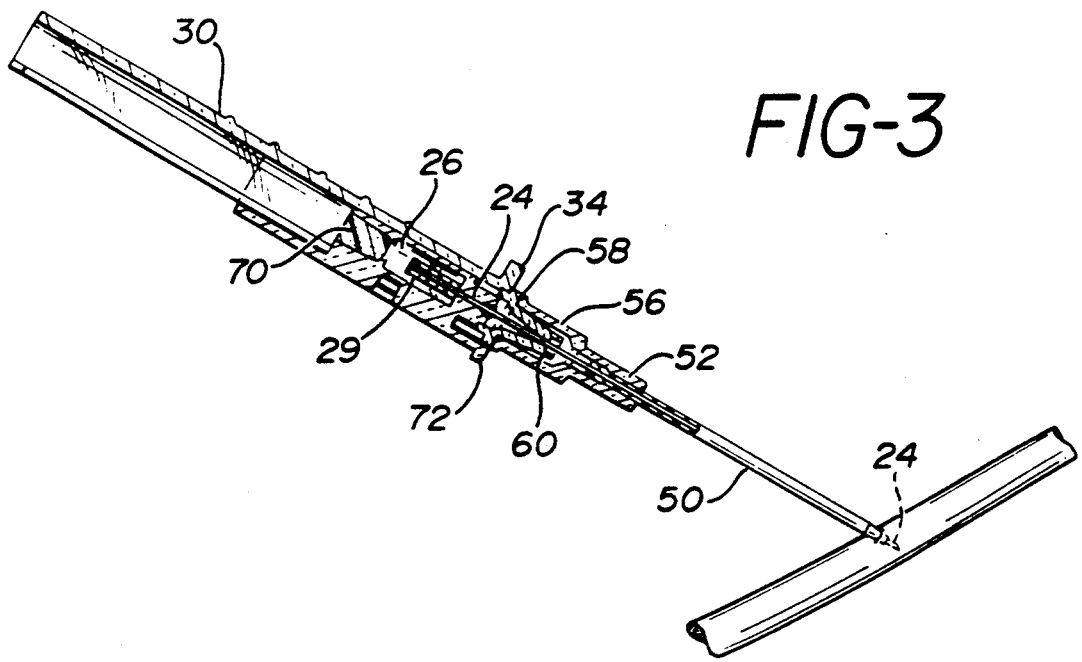
FIG. 3 is a simplified perspective view of a needle device containing the clear flash tube of the present invention upon initial insertion of the catheter needle.

Referring first to FIG. 1, a catheter assembly 10 constructed in accordance with the principles of the present invention is shown. The assembly 10 includes a needle housing 20 which is semi-tubular in shape and open at the top. Molded on the sides of the needle housing 20 are opposing contoured finger grips 22, one of which is visible in FIG. 1. Located inside the semi-tubular needle housing and extending proximally therefrom is a tubular needle guard 30. On the upper surface of the needle guard are a number of small projections 32 which provide surfaces against which a user may press to fully extend the needle guard. These projections permit a user to extend the needle guard with the index or other finger while holding the catheter assembly with one hand. Extending distally from the needle housing 20 is a protective sheath 40 which covers the distally extending needle and catheter at its distal end 48. Ribs 46 allow manipulation of sheath 40.

FIG. 2 illustrates the assembly of FIG. 1 after removal of the sheath 40. Projection 42 is separated from tabs 34, and detent 94 is pried from concentric ring 72, so that sheath 40 is removed. This drawing shows the catheter 50 and its catheter hub 52 mounted on the distal end of the needle guard 30. The point of the needle 24 is seen to extend from the distal tip of the catheter 50. A push-off tab 34 is seen projecting upward from the needle guard proximal the catheter hub 52.

Figure 4:
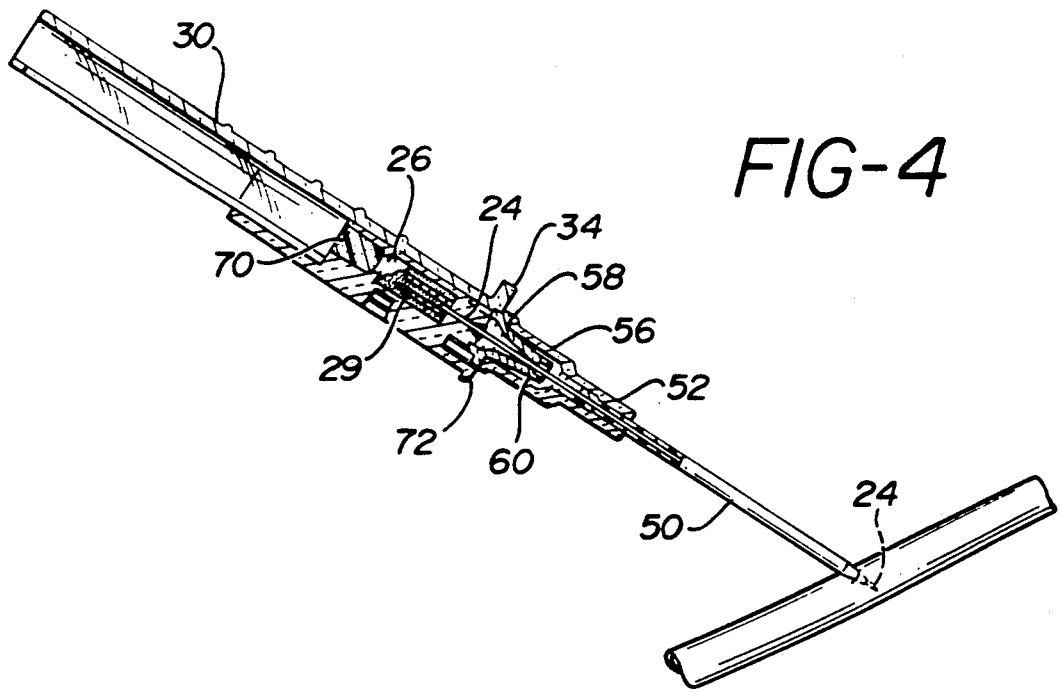
FIG. 4 is a simplified perspective view of the device as in FIG. 3 during insertion of the catheter needle into a vein with the flash chamber entirely filled.

As seen in FIGS. 2, 3 and 4 the needle 24 is attached to the distal end of the flash chamber 26 of the needle housing with the proximal end of the needle "24 affixed to needle hub 59 and " terminating with the chamber 26. The needle 24 is affixed in place by adhesive. The needle extends through a needle guard hub 58, which mates with catheter hub 52 as seen in FIG. 2. The needle guard tip 60 fits within catheter. hub 52, and the catheter 50, with the point of the needle extending from the distal end of the catheter. The rear of the flash chamber 26 is plugged by a microporous plug 70. The needle guard is seen to extend proximal the rear of the needle housing with the needle guard tip 60 affixed to the distal end of the needle guard at the location of the push-off tab 34. The tubular needle guard surrounds the flash chamber, 26, with the base 27 of the flash chamber being located in a longitudinal slot 36 at the bottom of the needle guard. As the needle guard slides in the distal direction to cover the needle it is maintained concentric with the needle housing by the concentric tubular construction of the needle housing and needle guard and by the tracking of the base 27 of the flash chamber 26 in the needle guard slot 36. Locking takes place at detent 92, which mates with a locking mechanism on housing 20.

As seen in FIGS. 3 and 4, this invention provides for a flash chamber design that suits the needs of both fast and slow flashback situations without one adversely affecting the performance of the other.

By adding a small clear tube 29 to the end of the needle 24 protruding into the flash chamber 26, the blood would travel through this tube 29 before entering the larger volume of the main flash chamber 24.

In the case of a small drop of flashback, it would elongate cylindrically along the inside of the tube 29 rather than form a spherical droplet on the end of the bore of the needle 24. With the tube 29 being clear, an optical effect occurs, and the visual size of the blood along the length of the tube 29 appears larger than only a droplet. The entire mass of the clear tube 29 appears to be red, when in fact, only the internal bore of the clear tube 29 is filled. This is best seen in FIG. 3.

The amount of blood required to fill up a clear tube 29 that is ½" in length, and attached to the end of a 26 gauge needle 24, such as in neonatal devices, and having an inside diameter to fit the needle, and an outside diameter of approximately 1/16", would be a droplet about 0.086" across. This amount of blood, when directed to flow inside this clear tube 29, will have a visibility profile 500 percent larger than if it was free to form a droplet on the end of the needle 24.

In cases where only a small droplet of flashback is produced, this tube 29 greatly enhances its apparent size and visibility. In cases where a large volume of flashback is encountered, the flashback would still be free to fill the remaining portion of the larger flash chamber 26 after initially passing through the clear tube 29. This latter situation is best seen in FIG. 4.

This configuration provides both the high visibility required for the low volume flashback cases, and the higher volume flash chamber needed for high volume flashback cases.

Therefore, during use the user inserts the catheter 50 and needle 24 in the vein. After the vein is punctured by the needle 24, blood quickly flows through the needle 24 and into the flash tube 29. Once blood appears on the flash tube 29 the user is certain of vein puncture and may begin to remove the needle 24 and have it lock in place against the locking section of the needle guard 30. The catheter remains in the patient and is attached to a I.V. connection. The enhanced visibility of the flash tube 29 in the flashback chamber 26 has therefore provided for a quick and efficient, as well as certain, flash determination.

It is to be understood that these and other objects of the invention are to be derived from the attached claims and their equivalents.

What is claimed is:

1. A catheter device containing:
    a catheter for insertion into a patient and having a tubular center into which is emplaceable an insertion needle;
    a needle hub and a hollow cylindrical insertion needle having a distal end for insertion into said catheter, and a proximal end engaged within said needle hub;
    a flash chamber connected to said needle hub and having a hollow interior, said insertion needle proximal end surrounded by said hollow interior; and
    a flash tube connected to said needle proximal end, said flash tube having an outer diameter and a length which permits said tube to fit within said flash chamber and said flash tube permitting blood to flow from a punctured vein through said needle and into said tube.

2. The catheter device of claim 1 wherein said flash chamber has a porous plug inserted, into an open end opposite said insertion needle.

3. The catheter device of claim 1 wherein said insertion needle is smaller than 25 gauge.

4. The catheter device of claim 1 wherein said flash tube and said flash chamber are formed from clear plastic.

5. The catheter device of claim 1 wherein said needle hub fits within a tubular needle guard, said needle guard slidable along said needle in order to fully enclose said needle within said needle guard, and said needle guard containing a needle guard hub; and
    wherein said catheter is connected to a catheter hub, said needle guard hub insertable into said catheter hub.

6. The catheter device of claim 5 wherein said needle guard locks against said needle hub when said needle guard slides along said needle to completely surround said needle.

7. A catheter device containing:
    a catheter for insertion into a patient and having a tubular center into which is emplaceable an insertion needle;
    a needle hub and a hollow cylindrical insertion needle having a distal end for insertion into said catheter, and a proximal end engaged within said needle hub;
    a flash chamber connected to said needle hub and having a hollow interior, said insertion needle proximal end surrounded by said hollow interior;
    a flash tube connected to said needle proximal end, said flash tube having an outer diameter and a length which permits said tube to fit within said flash chamber and said flash tube permitting blood to flow from a punctured vein through said needle and into said tube;
    a catheter hub to which said catheter is attached; and
    a needle guard containing a needle guard hub which fits in mating relationship with said catheter hub, said needle guard comprising a tubular cylinder which is capable of sliding over said needle hub and said needle in order to fully enclose said needle within said needle guard.

8. The catheter device of claim 7 wherein said flash chamber has a porous plug inserted into an open end opposite said insertion needle.

9. The catheter device of claim 7 wherein said insertion needle is smaller than 25 gauge.

10. The catheter device of claim 7 wherein said flash tube and said flash chamber are formed from clear plastic.

11. The catheter device of claim 7 wherein said needle guard locks against said needle hub when said needle guard slides along said needle to completely surround said needle.

12. An insertion needle assembly for emplacement in an intravenous catheter comprising:
    a hollow insertion needle having a sharpened distal end and a proximal end;
    a flash chamber with a hollow interior enclosing said needle proximal end; and
    a flash tube attached to said proximal end and contained within said flash chamber, said flash tube allowing fluid flow from said needle distal end, through said needle and tube, and into said flash chamber.

* * * * *